US009358049B2

(12) United States Patent
Simon et al.

(10) Patent No.: US 9,358,049 B2
(45) Date of Patent: *Jun. 7, 2016

(54) INTRAMEDULLARY NAIL AND IMPLANT SYSTEM COMPRISING THE NAIL

(71) Applicant: Stryker European Holdings I, LLC, Kalamazoo, MI (US)

(72) Inventors: Bernd Simon, Kiel (DE); Hendrik Klüver, Schönkirchen (DE); Martje Paulsen, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/682,457

(22) Filed: Apr. 9, 2015

(65) Prior Publication Data

US 2015/0209090 A1 Jul. 30, 2015

Related U.S. Application Data

(62) Division of application No. 13/763,858, filed on Feb. 11, 2013, now Pat. No. 9,072,552.

(30) Foreign Application Priority Data

Oct. 1, 2012 (EP) .................................. 12 006 837

(51) Int. Cl.

*A61B 17/84* (2006.01)
*A61B 17/58* (2006.01)
*A61B 17/72* (2006.01)

(Continued)

(52) U.S. Cl.

CPC ............... *A61B 17/742* (2013.01); *A61B 17/72* (2013.01); *A61B 17/7241* (2013.01); *A61B 17/744* (2013.01); *B23C 3/28* (2013.01);

(Continued)

(58) Field of Classification Search

CPC ... A61B 17/7241; A61B 17/72; A61B 17/744
See application file for complete search history.

(56) References Cited

U.S. PATENT DOCUMENTS 3,433,220 A 3/1969 Zickel
5,176,681 A 1/1993 Lawes et al.

(Continued)

FOREIGN PATENT DOCUMENTS

WO 2007038560 A1 4/2007
WO 2007048038 A2 4/2007
WO 2011044917 A1 4/2011

OTHER PUBLICATIONS

Orthopaedic Biomechanics Laboratory, Biomechanical Testing of Femoral Intramedullary Devices, pp. 1-14, Jun. 1996.

(Continued)

*Primary Examiner* — Jacqueline Johanas
(74) *Attorney, Agent, or Firm* — Lerner, David, Littenberg, Krumholz & Mentlik, LLP

(57) ABSTRACT

An intramedullary nail has a posterior side, an anterior side, a proximal portion and a distal portion is described. A transverse bore is arranged in the proximal portion and is configured to receive a bone engagement member. The transverse bore includes at least two recesses formed at an inner wall of the transverse bore, wherein one recess is arranged on the posterior side and the other recess is arranged on the anterior side of the transverse bore of the intramedullary nail.

17 Claims, 7 Drawing Sheets

(51) Int. Cl.

| | |
|---|---|
| ***A61B 17/86*** | (2006.01) |
| ***A61B 17/74*** | (2006.01) |
| ***B23C 3/28*** | (2006.01) |
| *A61B 17/00* | (2006.01) |

(52) U.S. Cl.

CPC .................. *A61B2017/00526* (2013.01); *Y10T 409/303808* (2015.01)

(56) References Cited

U.S. PATENT DOCUMENTS

| | | | |
|---|---|---|---|
| 5,454,813 | A | 10/1995 | Lawes |
| 5,733,287 | A | 3/1998 | Tepic et al. |
| 6,123,708 | A | 9/2000 | Kilpela et al. |
| 7,527,627 | B2 | 5/2009 | Ferrante et al. |
| 7,763,022 | B2 | 7/2010 | Speitling et al. |
| 7,780,667 | B2 | 8/2010 | Watanabe et al. |
| D638,125 | S | 5/2011 | Velikov |
| D638,126 | S | 5/2011 | Velikov |
| 8,034,056 | B2 | 10/2011 | Fencl et al. |
| 8,313,487 | B2 | 11/2012 | Tyber et al. |
| 8,328,806 | B2 | 12/2012 | Tyber et al. |
| 8,449,544 | B2 | 5/2013 | Grusin |
| 8,668,695 | B2 | 3/2014 | Schwammberger et al. |
| 2003/0171819 | A1 | 9/2003 | Sotereanos |
| 2004/0172027 | A1 | 9/2004 | Speitling et al. |
| 2006/0084999 | A1 | 4/2006 | Aschmann |
| 2006/0095039 | A1 | 5/2006 | Mutchler |
| 2006/0200160 | A1 | 9/2006 | Border et al. |
| 2006/0241604 | A1 | 10/2006 | Frigg et al. |
| 2008/0195098 | A1 | 8/2008 | Gotfried |
| 2008/0221574 | A1 | 9/2008 | Cavallazzi et al. |
| 2008/0249580 | A1 | 10/2008 | Evans et al. |
| 2009/0222049 | A1 | 9/2009 | Frigg et al. |
| 2010/0174284 | A1 | 7/2010 | Schwammberger et al. |
| 2010/0179551 | A1 | 7/2010 | Keller et al. |
| 2011/0160729 | A1 | 6/2011 | Overes et al. |
| 2012/0197255 | A1 | 8/2012 | Elghazaly |
| 2012/0265202 | A1 | 10/2012 | Schwammberger et al. |
| 2013/0274745 | A1 | 10/2013 | Kmiec, Jr. |
| 2014/0012259 | A1 | 1/2014 | Matityahu et al. |
| 2015/0272636 | A1* | 10/2015 | Schwammberger A61B 17/7241 606/62 |

OTHER PUBLICATIONS

Extended European Search Report for Application No. EP12006837 dated Feb. 8, 2013.

* cited by examiner

INTRAMEDULLARY NAIL AND IMPLANT SYSTEM COMPRISING THE NAIL

CROSS-REFERENCE TO RELATED APPLICATIONS

The present application is a divisional of U.S. patent application Ser. No. 13/763,858 filed Feb. 11, 2013, which claims priority from European Patent Application No. 006 837.4 filed Oct. 1, 2012, the disclosures of which are hereby incorporated herein by reference.

BACKGROUND OF THE INVENTION

The present disclosure generally relates to an intramedullary nail for internal fixation of a bone, such as a femur. The disclosure further relates to an implant system for use in orthopaedic surgery and to a method of manufacturing an intramedullary nail.

Femur fractures commonly occur in the femoral neck and the trochanteric regions. Today, trochanteric and sub-trochanteric femur fractures are treated with an intramedullary nail having a transverse bore in a proximal portion to receive a femoral neck screw usually provided in the form of a lag screw. Such a nail is shown in U.S. Pat. Nos. 5,176,681 and 5,454,813, the disclosures of which are incorporated herein by reference.

For fracture treatment the intramedullary nail is, in a first step, fitted in the intramedullary canal of the femur. Then the lag screw is passed through the transverse bore of the intramedullary nail, through the neck of the femur and into the femoral head. When implemented, a connecting fastener is inserted through a bore in a distal portion of the intramedullary nail to fasten the intramedullary nail to bone.

The lag screw is designed to transfer the load from the femoral head into a shaft of the nail while bridging the fracture line to allow fast and secure fracture healing. Further, the lag screw is allowed to slide in the intramedullary nail in accordance with the sintering of the femoral fracture.

U.S. Pat. No. 7,763,022 B2 relates to an intramedullary nail having a transverse bore for receiving a femoral lag screw at the proximal portion. The transverse bore has at an inlet opening a notch in form of an outer rounded edge. The notch ensures reduction of stress peaks in the end portions of the bore when the femoral lag screw is loaded (e.g., by the force of the patient's weight), specifically at the inlet opening.

U.S. 201000174284 relates to an intramedullary nail with a proximal portion including a cutout positioned adjacent to a transverse bore on the lateral side of the intramedullary nail.

U.S. Pat. Nos. 7,527,627 and 7,780,667 relate to an implant system with an intramedullary nail having a proximal transverse bore formed by two overlapping circular holes, wherein the proximal circular hole is smaller in diameter than a distal circular hole. The resulting 8-shaped transverse bore receives a fastener assembly comprising a lag screw used in conjunction with a compression screw.

It has been found that non-unions of peri and intratrochanteric fractures as well as sub-trochanteric fractures treated with an intramedullary nail can lead to overloading and thus breakage of the implant. Specifically, conventional intramedullary nails may be damaged at their smallest cross sectional area of the proximal portion, i.e., in the area of the transverse bore, for example during drilling with a lag screw step drill. Such a damage may lead to a weakening of the intramedullary nail in a critical area and result in brakeage of the implant when it is overloaded, (e.g., by the patient's weight). Moreover, the stability between the intramedullary nail and the femoral lag screw is decreased in such a situation and the implant system may fail to hold the fracture in a stable configuration, such that a well-defined compressive sliding of the femoral lag screw can no longer be guaranteed.

BRIEF SUMMARY OF THE INVENTION

Aspects of present disclosure are directed to the provision of an intramedullary nail and an implant system that facilitate a rapid healing of a femur fracture and results in a stable configuration of both the implant system and the fracture.

According to a first aspect, there is provided an intramedullary nail comprising, when implanted in the femur, a posterior side, an anterior side, a proximal portion, a distal portion and a transverse bore arranged in the proximal portion and configured to receive a bone engagement member. The transverse bore includes at least two recesses formed on an inner wall of the transverse bore, wherein one recess is arranged on the posterior side and the other recess is arranged on the anterior side of the transverse bore of the implanted intramedullary nail.

In one embodiment, each of the at least two recesses may define a length along the inner wall in a direction of a bore axis of the transverse bore. The length of each recess may be less than a length of the transverse bore along the bore axis.

The transverse bore has an inlet opening, wherein each of the at least two recesses may open out into the inlet opening of the transverse bore. Each of the at least two recesses may substantially extend in a direction of the bore axis of the transverse bore. Each of the at least two recesses may substantially extend from a lateral side towards a medial side of the intramedullary nail.

Each of the at least two recesses can have an oblique extension relative to an extension of the bore axis of the transverse bore. Further, each of the at least two recesses may be formed as a groove. In one implementation, each of the at least two recesses may be concave (e.g., V- or C-shaped) in cross-section. Moreover, each recess can have a crescent shape in cross section.

Each of the at least two recesses may define an arc segment in cross-section which extends over an angle with respect to the bore axis of the transverse bore. The angle can lie between 5° and 175°. The angle may specifically lie between 20° and 100°. Further, each of the at least two recesses may define an arc segment in cross-section, wherein each recess has a width along the arc segment which lie between 1 mm and 10 mm. For example, the width along the arc segment may lie between 3 mm and 8 mm.

The transverse bore may define a first diameter which is oriented substantially parallel to a longitudinal axis of the proximal portion and a second diameter which is oriented substantially perpendicular to the longitudinal axis of the proximal portion, wherein the second diameter is greater than the first diameter in at least a portion of the transverse bore. Further, the transverse bore may define a bore axis which is oriented obliquely with respect to the longitudinal axis of the proximal portion.

In one embodiment, the at least two recesses of the transverse bore may be arranged adjacent to each other on opposite sides of the bore axis of the transverse bore. The transverse bore can have one of flattened and rounded edge portions in a region of at least one of an inlet opening and an outlet opening. Further, the intramedullary nail can include a cannulation or channel substantially along a longitudinal axis of the intramedullary nail.

According to a further aspect, there is provided an implant system for use in orthopaedic surgery for fixation of bone.

The implant system comprises an intramedullary nail as generally configured and described above and hereinafter, and a bone fastener configured to penetrate the transverse bore of the intramedullary nail In the aspect described above, the transverse bore of the intramedullary nail may define a bore axis which is substantially parallel to or congruent with a longitudinal axis of the bone fastener. Further, the bone fastener can be a sliding screw (e.g., a lag screw or femoral neck screw) configured to be slidably received within the transverse bore of the intramedullary nail.

According to a further aspect, there is provided a method of manufacturing an intramedullary nail having a posterior side, an anterior side, a proximal portion, a distal portion and a transverse bore arranged in the proximal portion and configured to receive a bone engagement member. The method comprises the step of guiding a milling tool for producing at least two recesses formed at an inner wall of the transverse bore in such a way that one recess is arranged on the posterior side and the other recess is arranged on the anterior side of the transverse bore of the intramedullary nail.

As used herein when referring to bones or other parts of the body, the term “proximal” means close to the heart and the term “distal” means more distant from the heart. The term “inferior” means toward the feet and the term “superior” means toward the head. The term “anterior” means toward the front part or the face and the term “posterior” means toward the back of the body. The term “medial” means toward the midline of the body and the term “lateral” means away from the midline of the body.

BRIEF DESCRIPTION OF THE DRAWINGS

The above and other features, aspects and advantages of the present disclosure will become apparent from the following detailed description taken in conjunction with the accompanying drawings, wherein.

DETAILED DESCRIPTION

Figure 1:
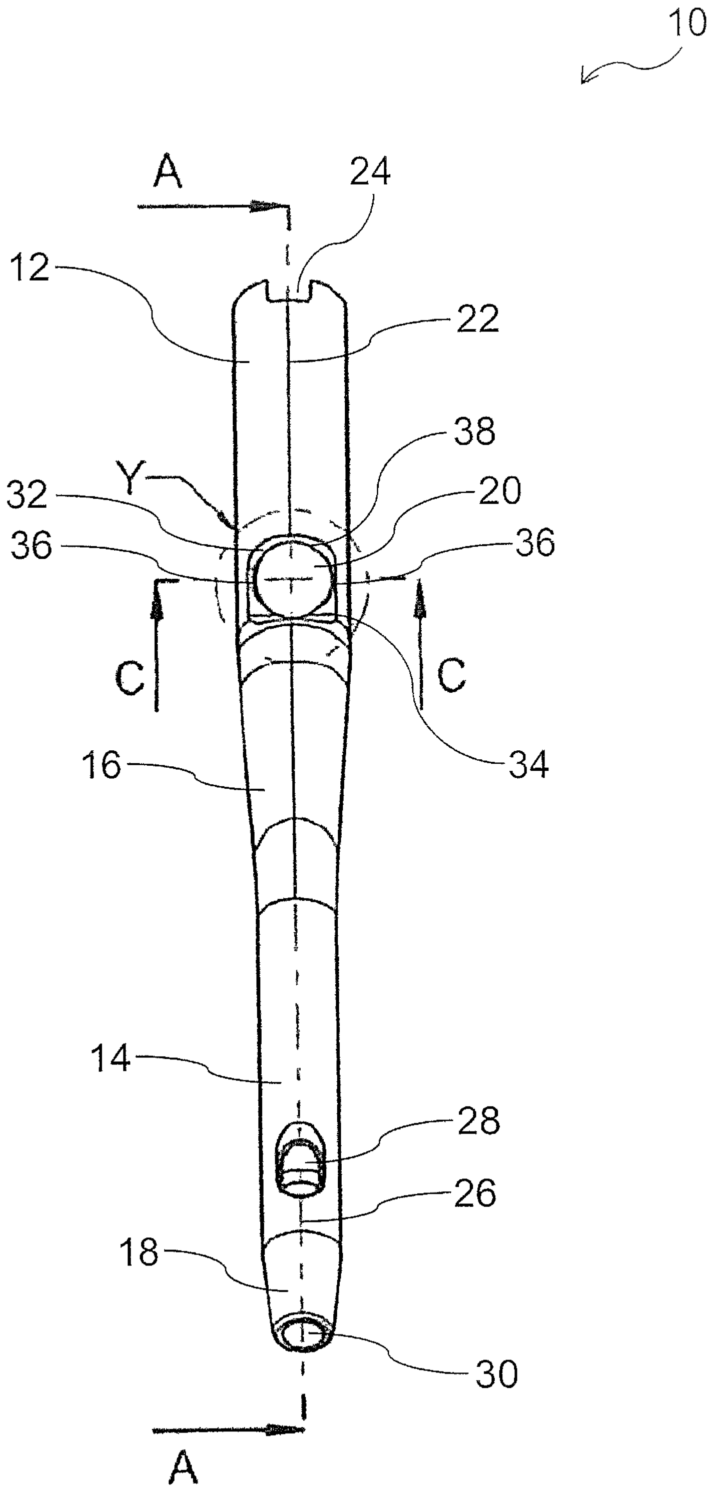
FIG. 1 is a lateral side perspective view of an intramedullary nail embodiment showing the transverse bore inlet.

In the following description of exemplary embodiments, the same or similar components will be denoted by identical reference numerals. It will be appreciated that while the following embodiments will primarily be described with respect to the treatment of a femur, the implant presented herein, with suitable modifications, could also be used for treatment of other bones.

Referring to FIG. 1, there is shown a lateral side view of an embodiment of an intramedullary nail 10 for use in orthopaedic surgery for fixation of bone, such as a femur (not shown in FIG. 1). The intramedullary nail 10 is made of a biocompatible material such as stainless steel, titanium or a titanium alloy. The intramedullary nail 10 includes a rod-shaped body insertable into the inner cavity of a bone (marrow cavity), e.g., into the intramedullary canal of a femur.

The intramedullary nail 10 includes a proximal portion 12, a distal portion 14 and an intermediate portion 16 therebetween. Thus, the intermediate portion 16 connects the proximal portion 12 with the distal portion 14. As shown in FIG. 1, the intramedullary nail 10 tapers in a direction from the proximal portion 12 to the distal portion 14. The distal portion 14 is longer than the proximal portion 12. The intermediate portion 16 located between the proximal portion 12 and the distal portion 14 is bent for anatomical reasons.

The intramedullary nail 10 has a substantially circular cross-section over its entire length. The proximal portion 12 and the distal portion 14 of the intramedullary nail 10 have a substantially cylindrical shape. The proximal portion 12 of the intramedullary nail 10 has a diameter sufficient to accommodate a transverse bore 20 therein. While in the present embodiment only a single transverse bore 20 is present, in other embodiments multiple (e.g., two or more) similar transverse bores may be provided in the proximal portion 12. The distal portion 14 has a smaller diameter than the proximal portion 12, adapted to the shape of the marrow cavity of the femur in order to facilitate the insertion of the distal portion 14 into the intramedullary canal. For the same reason, the distal portion 14 has a conical tip portion 18 at its distal end. The intermediate portion 16 connecting the proximal portion 12 and the distal portion 14 substantially tapers in a direction from the proximal portion 12 to the distal portion 14.

The proximal portion 12 of the intramedullary nail 10 defines a longitudinal axis 22 and includes a connecting portion in form of a recess 24 for receiving an end cap or a surgical tool, such as a holding instrument or targeting instrument (not shown in FIG. 1) at the upper rim of the proximal portion 12. The distal portion 14 likewise defines a longitudinal axis 26 which is angled with respect to the longitudinal axis 22 of the proximal portion 12. Further, the distal portion 14 includes an opening 28 in form of an elongated through hole. The elongated through hole 28 is formed at an end of the distal portion 14 of the intramedullary nail 10 for receiving a bone fastener, such as a connecting fastener (e.g., a locking screw). The bone fastener is used to fasten and securely fix the intramedullary nail 10 to bone.

Further, the intramedullary nail 10 has a cannulation channel 30 axially extending through the intramedullary nail 10. The channel 30 may receive a surgical wire (not shown in FIG. 1), such as a Kirschner wire, for guiding the intramedullary nail 10 to and through the bone.

As shown in FIG. 1, the transverse bore 20 located at the proximal portion 12 has flattened and rounded edge portions 32 and 34. Further, the transverse bore 20 includes two recesses 36, or pockets, formed at an inner wall 38 of the transverse bore 20. Each of the two recesses 36 substantially extends along the transverse bore 20. In the present case, each of the two recesses 36 substantially extends from a lateral side towards a medial side of the intramedullary nail 10 and may extend completely through the bore.

The terms medial and lateral are standard anatomical terms of direction and denote a direction toward the center of a median plane of a body and the opposite direction from the center to the side, respectively. With respect to the present disclosure and the exemplary embodiments, the medial and lateral directions may generally lie within a plane including the longitudinal axis 22 of the proximal portion 12 (or the longitudinal axis of the intramedullary nail 10) and an axis of the transverse bore 20. In such a case, the medial side of the intramedullary nail 10 may be a side facing towards the outgoing side of the transverse bore 20 (e.g., towards a tip of a bone engagement member penetrating the transverse bore 20), whereas the lateral side may be a side facing towards the ingoing side of the transverse bore 20 (e.g., towards a head of the bone engagement member). In the present exemplary case, the intramedullary nail 10 is anatomically shaped so that the intramedullary nail 10 inherently defines the medial and lateral sides, for example with respect to its bent portion (e.g., as embodied by the bent intermediate portion 16 of the intramedullary nail 10) resulting in an inclination of the transverse bore 20.

Figure 2:
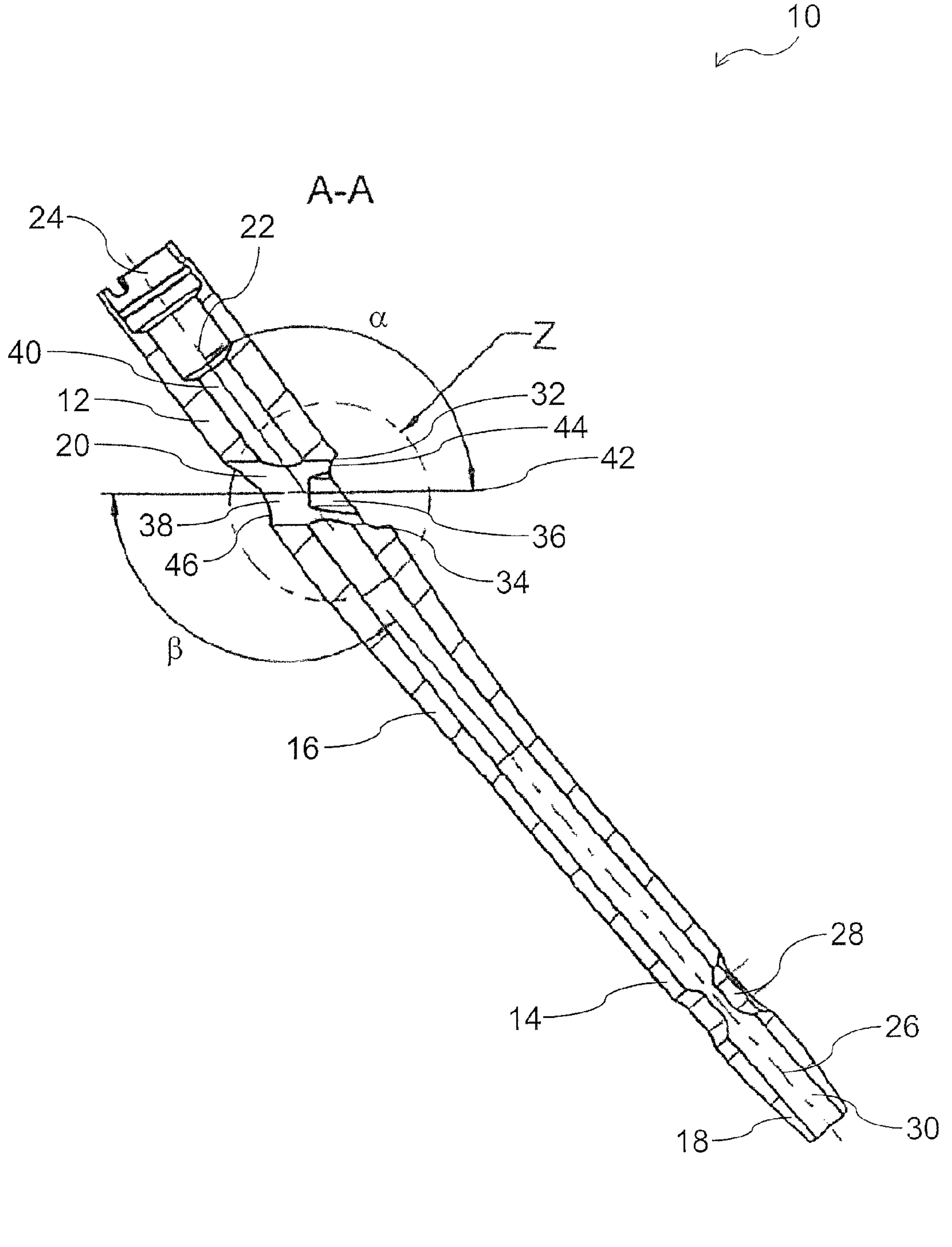
FIG. 2 is a cross-sectional view of the intramedullary nail embodiment taken along line A-A in FIG. 1.

FIG. 2 shows a cross-sectional view of the intramedullary nail embodiment shown in FIG. 1 along the line A-A, i.e., along an imaginary longitudinal axis of the intramedullary nail 10. As shown in FIG. 2, the proximal portion 12 of the intramedullary nail 10 includes a compartment 40 for reception of an interlocking pin or set screw (both not shown in FIG. 2) that engages a bone engagement member received by the transverse bore 20. In the present embodiment, the compartment 40 of the proximal portion 12 is co-axial with the longitudinal axis 22 of the proximal portion 12. The compartment 40 may include an internal thread which mates with a corresponding thread of a set screw. As further shown in FIG. 1, the compartment 40 opens out in a distal direction into the transverse bore 20 of the proximal portion 12.

Still referring to FIG. 2, a bore axis 42 of the transverse bore 20 is angled with respect to the longitudinal axis 22 of the proximal portion 12, such that the longitudinal axis 22 of the transverse bore 20 has an oblique extension relative to an axial extension of the proximal portion 12. In other words, the bore axis is oriented obliquely with respect to the longitudinal axis 22 of the proximal portion 12. Thus, the bore axis 42 of the transverse bore 20 is inclined at an angle α with respect to the longitudinal axis 22 of the proximal portion 12. The bore axis 42 of the transverse bone 20 is further inclined at an angle β with respect to the longitudinal axis 26 of the distal portion 14. These angles α and β may lie between 50° and 150°. For example, the angle α of the bore axis 42 of the transverse bore 20 with respect to the longitudinal axis 22 of the proximal portion 12 may lie between 90° and 140°. Further, the angle β of the bore axis 42 of the transverse bore 20 with respect to the longitudinal axis 26 of the distal portion 26 may lie between 90° and 140° as well. In the present embodiment, the angle α is approximately 126° and the angle β is approximately 130°.

As further shown in FIG. 2, the transverse bone 20 of the proximal portion 12 substantially extends in a direction from a lateral side to a medial side of the intramedullary nail 10. The transverse bore 20 has an inlet opening 44 and an outlet opening 46 for the bone engagement member (not shown in FIG. 2). The inlet opening 44 faces away from the head of the femur when the intramedullary nail 10 has been driven into the bone canal. As shown in FIG. 2, each of the two recesses 36 opens out into the inlet opening 44 of the transverse bore 20.

Figure 3:
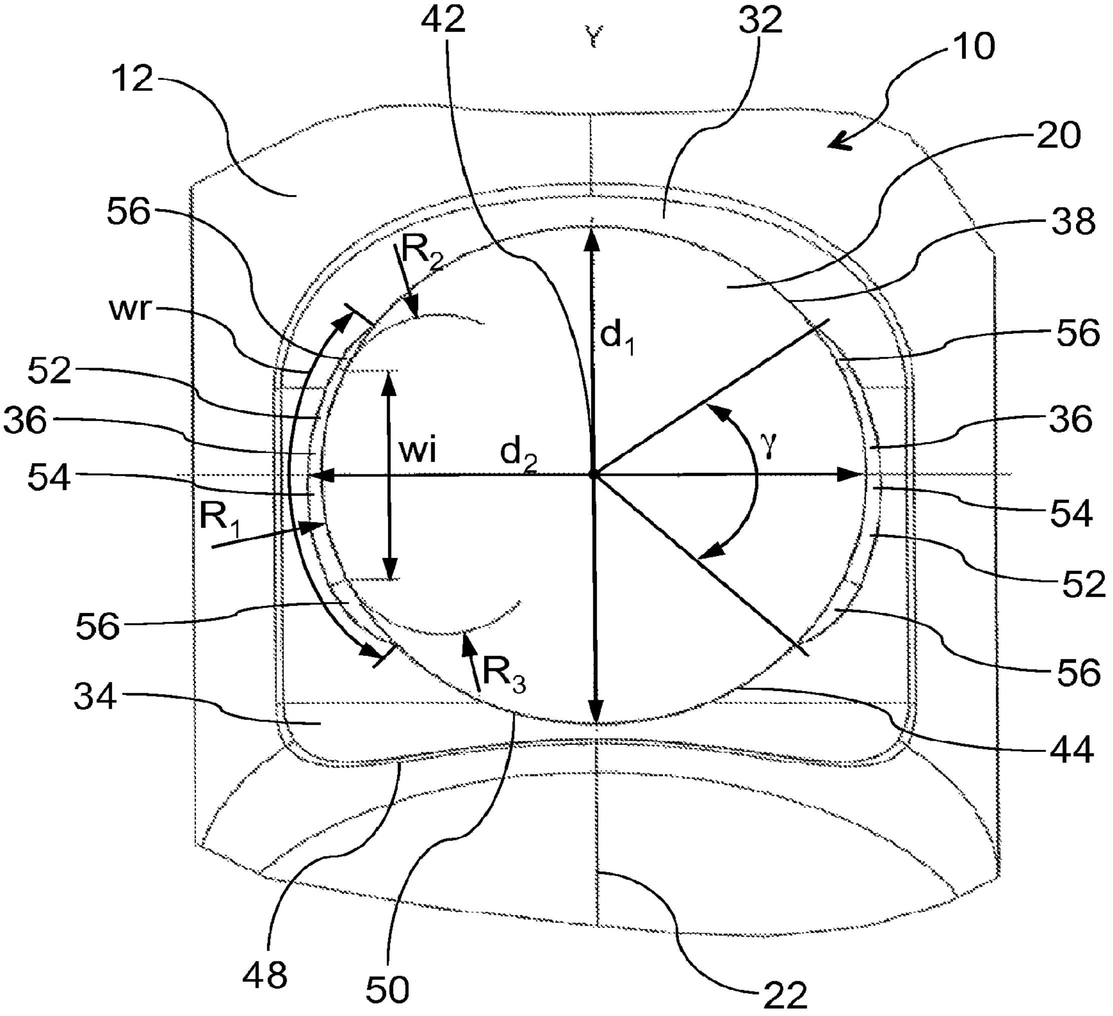
FIG. 3 is an enlarged view of detail Y of the intramedullary nail embodiment shown in FIG. 1.
Figure 4:
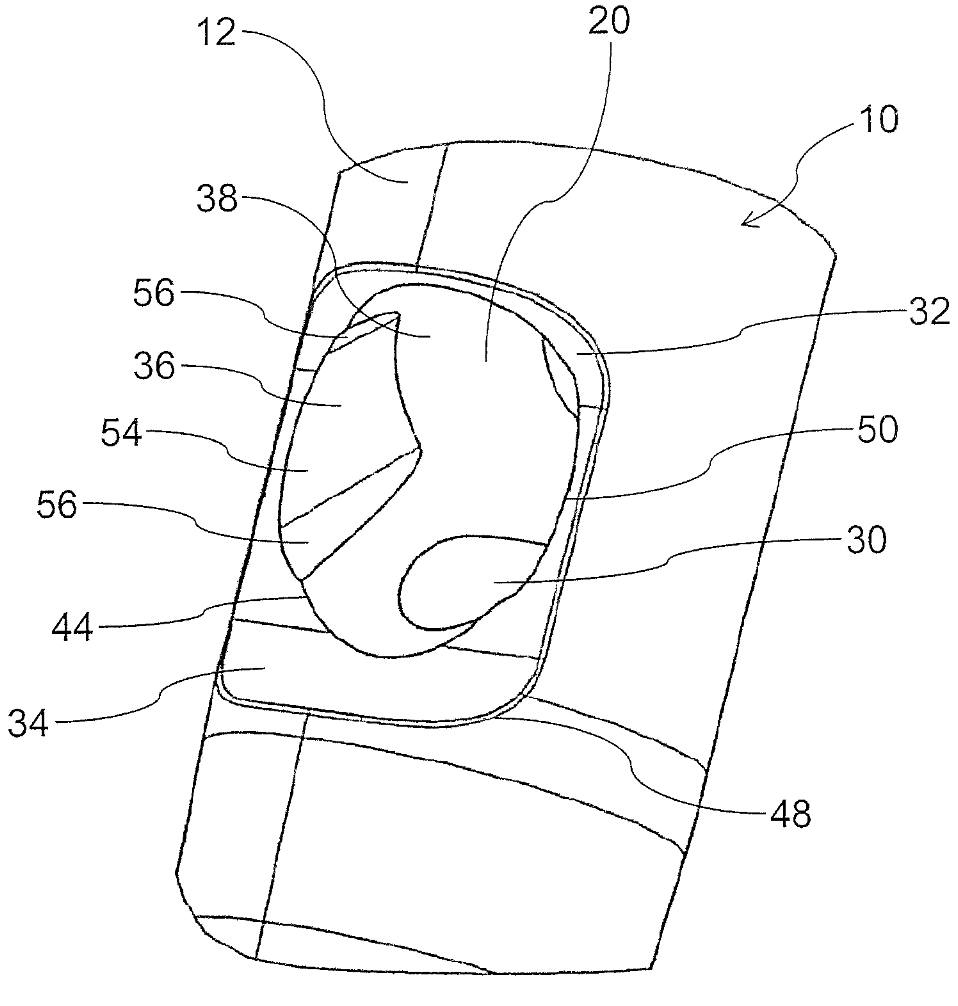
FIG. 4 is a perspective side view of the proximal portion of the intramedullary nail embodiment shown in FIG. 1.

FIG. 3 illustrates a detailed side view of the transverse bore 20 of the proximal portion 12 denoted by Y in FIG. 1. FIG. 4 illustrates a perspective view thereof.

As shown in FIGS. 3 and 4, the inlet opening 44 opens out into a notch, or depression, defined by the outer rounded edge 32 and the flattened edge 34. The depression has an approximately square contour with rounded corners. An outer edge 48 of the depression is located in the outer contour of the proximal portion 12. An inner edge 50 of the depression is located within the outer edge 48 and defines the inlet opening 44. As illustrated in FIGS. 3 and 4, surface portions which partially are beveled or chamfered are formed between the outer edge 48 and the inner edge 50 of the notch.

As illustrated in FIG. 3, each of the recesses 36 has generally a concave shape in cross-section. Further, one of the two recesses 36 is arranged on the posterior side (e.g., the left side in FIG. 3) and the other recess 36 is arranged on the anterior side (e.g., the right side in FIG. 3) of the intramedullary nail 10, i.e., on the posterior side and the anterior side of the transverse bore 20, respectively. In other words, the two recesses 36 of the transverse bore 20 are arranged across from each other on opposite sides of the bore axis 42 of the transverse bore 20.

The terms anterior and posterior are standard anatomical terms of direction and denote a direction toward the front of a body (ventral) and the opposite direction toward the back of the body (dorsal), respectively. With respect to the present disclosure and the exemplary embodiments, the anterior and posterior directions may generally lie within a plane including the longitudinal axis 22 of the proximal portion 12 and a diameter of the transverse bore 20. In many cases, an intramedullary nail will be anatomically configured so that the intramedullary nail inherently defines the anterior and posterior sides.

As illustrated in FIG. 3, each recess 36 formed at the inner wall 38 of the transverse bore 20 defines an arc segment 52 in cross-section. The arc segment 52 of each recess 36 extends over an angle γ with respect to the bore axis of the transverse bore 20. The angle γ of the arc segment 52 can lie between 5° and 175°. For example, the angle γ of the arc segment may lie between 45° and 120°, and is in the present embodiment approximately 80°. Further, each of the two recesses 36 has a width wr along the arc segment 52. The width wr along the arc segment 52 of each recess 36 may between 2 mm and 14 mm. In the present embodiment, the width wr is approximately 8 mm.

As further illustrated in FIGS. 3 and 4, each arc segment 52 is defined by three (or, in other embodiments, more or less) radii $R_1$, $R_2$ and $R_3$ which define the concave shape of the recess 36. Thus, the cross-section of each recess 36 can be divided into three regions separated from each other along the arc segment. As illustrated in FIGS. 3 and 4, each recess 36 has an intermediate region 54 and two outer regions 56 adjacent thereto. The intermediate region 54 of the recess 36 is defined by a circle which has a radius $R_1$. The radius $R_1$ can lie between 1.0 mm and 20.0 mm, preferably between 3.0 mm and 10.0 mm, and is in the present embodiment approximately 5.2 mm. The outer regions 56 of each recess 36 are defined by a radius $R_2$ and radius $R_3$ respectively. The radii $R_2$ and $R_3$ can be different from each other or, as in the present embodiment, equal. The radii $R_2$ and $R_3$ can lie between 1.0 mm and 20.0 mm, preferably between 1.0 mm and 7.0 mm, and are both in the present embodiment approximately 2.0 mm.

As further illustrated in FIG. 3, the transverse bore 20 defines a first diameter $d_1$ which is oriented substantially parallel to the longitudinal axis 22 of the proximal portion 12 (i.e., the first diameter $d_1$ is oriented in a direction from the proximal side to the distal side of the intramedullary nail 10). The transverse bore 20 further defines a second diameter $d_2$ which is oriented substantially perpendicular to the longitudinal axis 22 of the proximal portion 12 (i.e., the second diameter $d_2$ is oriented in a direction from a posterior side to the anterior side of the intramedullary nail 10). As shown in FIGS. 3 and 4, the second diameter $d_2$ is greater than the first diameter $d_1$ in at least a portion of the transverse bore 20. In the present embodiment, the second diameter $d_2$ is greater than the first diameter $d_1$ (i.e., in the lateral/medical plane of the intramedullary nail 10).

Figure 5:
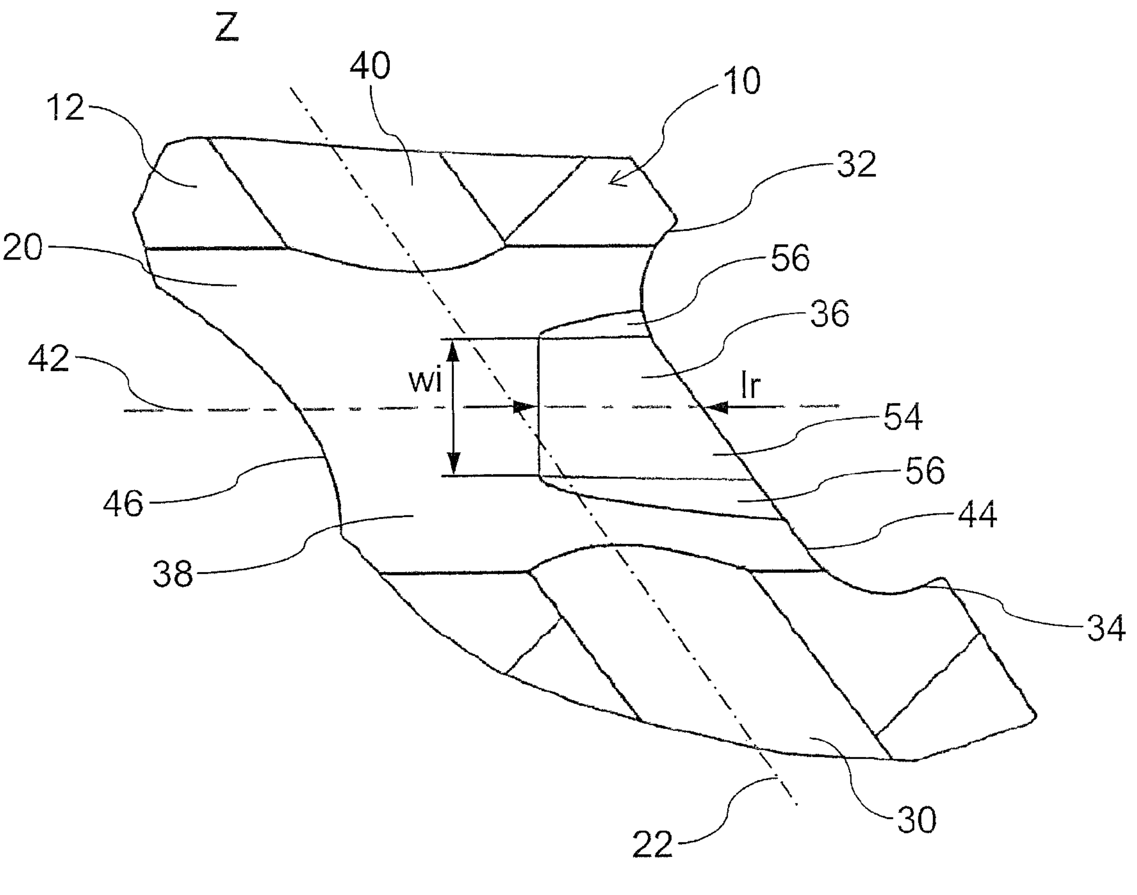
FIG. 5 is a view of detail Z of the intramedullary nail embodiment shown in FIG. 2.

FIG. 5 shows a detailed cross-sectional view of the transverse bore 20 of the proximal portion 12 denoted by Z in FIG. 2. In FIG. 5, as well as in FIG. 2, the lateral side of the intramedullary nail 10 is on the right side and the medial side of the intramedullary nail 10 is on the left side of the drawing.

As illustrated in FIG. 5, each of the two recesses 36 defines a length lr along the inner wall 38 in a direction of the bore axis 42 of the transverse bore 20. In the present embodiment, the length lr of each recess 36 is less than the length of the transverse bore 20 along the bore axis 42. The length lr of each recess 36 may lie between 1 mm and 10 mm, preferably between 2 mm and 7 mm, and is approximately 5.3 mm in the present embodiment. As illustrated in FIG. 5 and as well as in FIG. 3, the intermediate region 54 of each recess defines a width wi which is oriented in a direction substantially perpendicular to the bore axis 42. In other words, the width wi of the intermediate region 54 of the recess 36 is oriented substantially parallel to the longitudinal axis 22 of the proximal portion 12. The width wi of each recess 36 may lie between 2 mm and 9 mm, preferably between 3 mm and 5 mm. In the present embodiment, the width wi of the intermediate region 54 of each recess 36 is approximately 4.4 mm.

As shown in FIGS. 4 and 5, each of the two recesses 36 has an oblique extension relative to an extension of the bore axis 42 of the transverse bore 20. In the present embodiment, the outer regions 56 of the recess 36 taper towards the center line of the bore in a direction from the inlet opening 44 toward the outlet opening 46 of the transverse bore 20 (in this case, in the plane of the drawing of FIG. 5).

Figure 6:
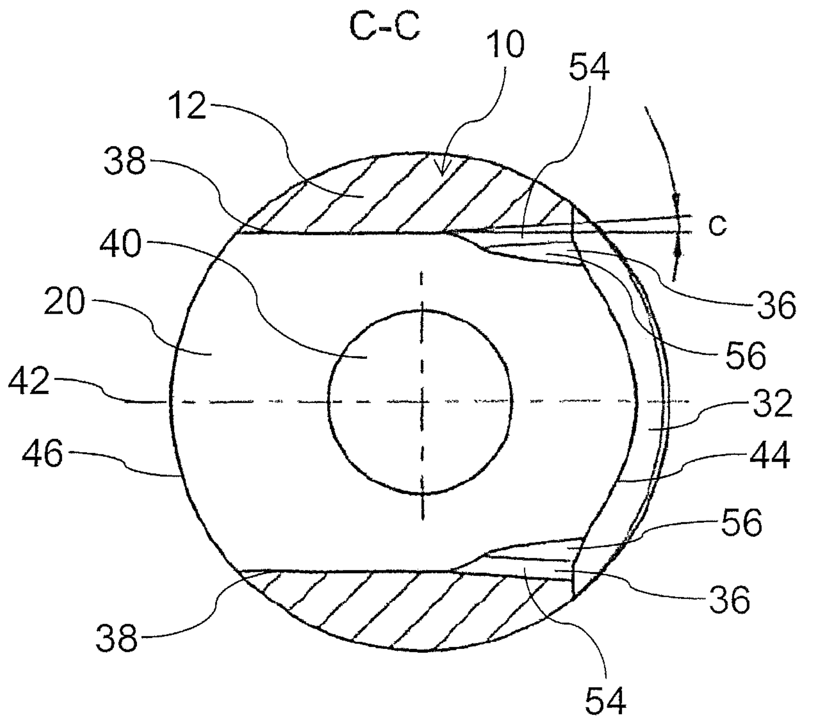
FIG. 6 is a cross-sectional view of the intramedullary nail embodiment taken along line C-C in FIG. 1.

FIG. 6 illustrates a cross sectional view of the transverse bore 20 of the proximal portion 12 along line C-C shown in FIG. 1. As becomes apparent in FIG. 6, each recess 36 has a conical shape in the direction of the bore axis 42 of the transverse bore 20 (in this case, in the plane of the drawing of FIG. 6). Each recess 36 defines a taper with a cone angle c with respect to the inner wall 38 of the transverse bore 20. The cone angle c can lie between 1° and 10°, preferably between 2° and 5°. In the present embodiment, the cone angle c of each recess 36 is approximately 3.8°.

As shown in FIG. 6, the cone angle c lies within a plane including the bore axis 42 of the transverse bore 20 and the diameter $d_2$ of the transverse bore 20 (i.e., a plane which is perpendicular to the longitudinal axis 22 of the proximal portion 12). Each recess 36 tapes substantially in a direction from the inlet opening 44 toward the outlet opening 46 of the transverse bore 20. Thus, the recesses 36 widen in a direction toward the inlet opening 44 of the transverse bore 20. In the present embodiment as shown in FIGS. 5 and 6, the two recesses 36 widen the transverse bore 20, on the one hand, in a direction of the bore axis 42 of the transverse bore 20 and, on the other hand, in a direction of the longitudinal axis 22 of the proximal portion 12, in both cases, toward the inlet opening 44 of the transverse bore 20.

It has been found that the recesses 36 help to reduce the probability of nail breakage in the region of the transverse bore 20. Especially in cases in which the inner wall 38 of the transverse bore 20 gets damaged (e.g., by a drill operation through the transverse bore 20) the rate of nail breakages can be reduced. This reduction can be attributed to smaller material tensions in a region of the intramedullary nail 10 around the transverse bore 20 due to the presence of recesses 36.

Figure 7:
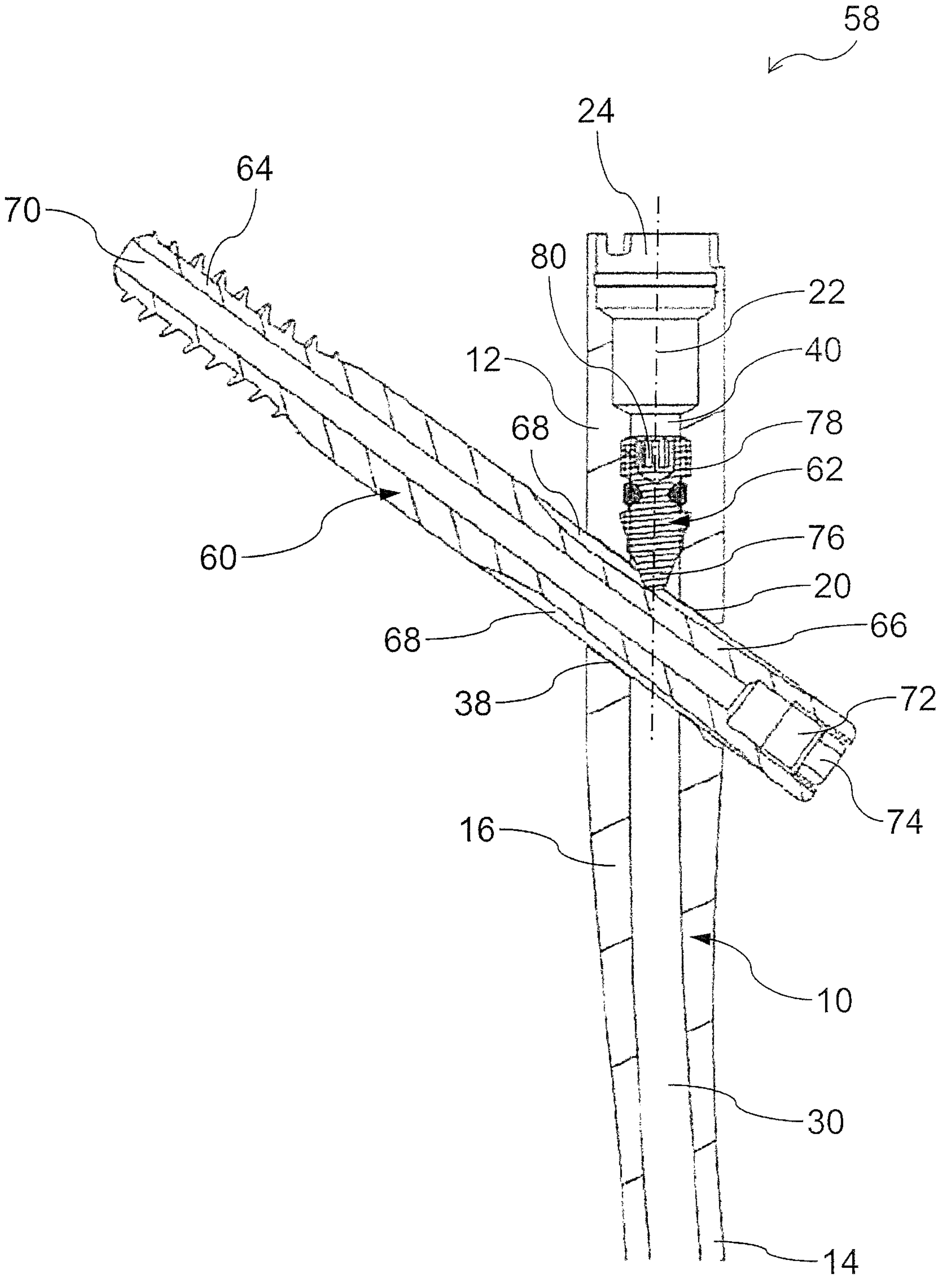
FIG. 7 is a cross-sectional view of an implant system embodiment that is based on the intramedullary nail embodiment shown in FIGS. 1 and 2.

Now referring to FIG. 7, there is shown a cross-sectional view of an embodiment of an implant system 58 for use in orthopaedic surgery for fixation of bone, such as a femur (not shown in FIG. 7). The implant system 58 comprises the intramedullary nail 10 as described above with reference to FIGS. 1 to 6. The implant system 58 further includes a bone fastener 60 (that forms a bone engagement member) and a coupling unit 62 which may be an anti-rotation screw which permits compressive sliding. The bone fastener 60 is configured to penetrate the transverse bore 20 of the intramedullary nail 10 from the inlet opening 44 to the outlet opening 46. The coupling unit 62 couples the bone fastener 60 to the intramedullary nail 10.

In the embodiment shown in FIG. 7, the bone fastener is a sliding screw (e.g., femoral neck screw or lag screw), with a front portion 64 including a thread, for example a coarse thread, and a rear portion 66. The rear portion 66 is provided with a plurality of longitudinally extending grooves 68 (two are shown in FIG. 7) arranged on the peripheral surface of the rear portion 66 along a longitudinal axis of the sliding screw 60. In the present realization, four grooves 68 are disposed on the peripheral surface of the sliding screw 60 at intervals of 90° around the longitudinal axis of the sliding screw 60. Each groove 68 defines a ramp having a shallow end and a deeper end. The rising ramp extends from the end of the rear portion 66 towards the threaded front portion.

Further, the sliding screw 60 includes a central cannulation 70 along the longitudinal axis of the sliding screw 60. The rear portion 66 of the sliding screw 60 includes at its free end a co-axial bore 72 and a recess 74 (e.g., a hexalobular internal driving feature) for receiving a tool tip (e.g., of screw driver or a wrench).

As shown in FIG. 7, the unthreaded rear portion 66 of the sliding screw 60 is slidably received in the transverse bore 20 of the proximal portion 12 of the intramedullary nail 10. Further, the bore axis 42 of the transverse bore 20 is substantially parallel to the longitudinal axis of the sliding screw 60. In the present embodiment the bore axis 42 is congruent with the longitudinal axis of the sliding screw 60. The sliding screw 60 can thus transfer the load of the femoral head into the intramedullary nail 10 and at the same time bridges the fracture line to allow fast and secure fracture healing.

As further shown in FIG. 7, the coupling unit 62 is realized as a set screw which is preassembled and movably arranged within the proximal portion 12 of the intramedullary nail 10. The coupling unit 62 includes one bone fastener engagement member 76 and a drive member 78. In the present embodiment, the engagement member 76 of the coupling unit 62 is centrally positioned within the bore 40 of the proximal portion 12. Further, the engagement member 76 is realized in the exemplary form of a substantially cylindrical bolt, pin or protrusion. The drive member 78 of the coupling unit 62 is connected to the engagement member 76 and includes an external thread for threadable engagement with the intramedullary nail 10 (e.g., with the proximal portion 12 as shown in FIG. 7). The bore 40 of the proximal portion 12 includes an internal thread which mates with the external thread of the drive member 78 of the coupling unit 62. In the present embodiment, the drive member 76 of the coupling unit is movably arranged within the bore 40 of the proximal portion 12 of the intramedullary nail 10. Moreover, the coupling unit 62 is captively held within the proximal portion 12 of the intramedullary nail 10. As illustrated in FIG. 7, the engagement member 76 of the coupling unit 62 can engage within a groove 68 of the sliding screw 60. Upon engagement within the groove 68, the engagement member 76 can exert pressure on the sliding screw 60 for stabilization purposes. The pressure is initially zero or low enough to still permit a sliding movement of the sliding screw 60 relative to the intramedullary nail 10. The pressure will change (and typically increase) as the sliding screw 60 slides due to the depth profile (i.e., the lateral and medial ramps) of the grooves 68.

Rotation of the drive member 78 of the coupling unit causes movement of the engagement member 76 along the longitudinal axis 22 of the proximal portion 12. For this propose, the drive member 78 of the coupling unit 62 has a receiving portion 80 in form of a recess (e.g., realized as a hexalobular internal driving feature) for receiving a tool such as a screw driver or wrench. By driving the drive member 78 using such a tool, the entire coupling unit 62 moves along the longitudinal axis 22 of the proximal portion 12 of the intramedullary nail 10, since the external thread of the drive member 78 mates with the internal thread of the bore 40 of the proximal portion 12. In other words, the position of the coupling unit 62, and thus the position of its engagement member 76, within the proximal portion 12 of the intramedullary nail 10 can be adjusted by screwing the drive member 78 of the coupling unit 62 along the longitudinal axis 22 of the proximal portion 12.

An embodiment of a manufacturing process for modifying a notch (or depression) formed around the neck screw bore (i.e., the transverse bore arranged in the proximal portion of the intramedullary nail) will now be described. The process may be performed before or after the notch is formed around the predrilled femoral neck screw bore in accordance with, for example, the aforementioned U.S. Pat. No. 7,763,022 B2. The process may also be performed without formation of such a notch. A cone shaped pocket, i.e., a recess 36, is formed on both the anterior and posterior side of the bore although the formation of only one cone-shaped pocket will be described.

In a first step a central axis of a mill cutter head is aligned with the axis 42 of the neck screw bore 20 (i.e., the transverse bore 20 of the proximal portion 12 of the nail 10). For example, the bore 20 may be angled at about 126° to the longitudinal axis 22 of the proximal portion 12 of the intramedullary nail 10. The mill cutter axis is placed at the neck screw entry side (i.e., the lateral side) of the intramedullary nail 10 and is then angled in at least one plane, for example at an angle of about 3.8° to a first plane containing both the proximal nail axis 22 and the neck screw bore axis 42. The cutter head is then moved in two elliptical paths to form a conically tapered recess 36 having a curved inwardly facing surface. The curved surface extends proximally and distally of a second plane containing the axis 42 of the screw bore 20 and perpendicular to the first plane. The proximal and distal foci of the two ellipses are located, for example, about 1.2 mm proximal and about 2.2 mm distal of the second plane. The curved surface is formed by moving the mill head along a spline connecting end portions of the two ellipses since the foci are spaced at different distances from the first plane. The mill head cutting path forms a tangent with each ellipse end portion.

While in the embodiments illustrated in the drawings the rod-shaped body of the intramedullary nail includes a distal portion, a proximal portion and an intermediate (bent) portion therebetween, the nail body can be adapted as needed (e.g., in terms of shape, length, width, thickness, etc.) for use in orthopaedic surgery for fixation of bone and for insertion into an intramedullary canal of, e.g., a femur. Thus, the shape of the intramedullary nail can be adapted to different applications.

While the bone engagement member (bone fastener) described herein is formed as a sliding screw or a lag screw, the bone engagement member can be of any type (e.g., a femoral neck screw or any kind of blade) and can be adapted to different applications as needed. Furthermore, one or more bone engagement members (e.g., two, three or more bone fasteners) may be arranged in the constellation as shown in and described with reference to FIG. 7. In other words, the implant may have two or more transverse openings and two or more sliding screws arranged therein in a manner as shown in FIG. 7. The bone engagement members as well as the connecting fastener(s) may have different diameters, lengths, shapes or threads.

While the above embodiments have exemplarily been described in relation to bone screws and an intramedullary nail, it will be readily apparent that the techniques presented herein can also be implemented in combination with other or further types of bone fasteners (such as bone pegs having a rod-like or pin-like shaft, wire-like bone fasteners such as Kirschner wires, etc.). Accordingly, the present disclosure is not limited to any type of bone fastener.

The features described in the above description taken in conjunction with the accompanying drawings can be readily combined to result in different embodiments. It will thus be apparent that the present disclosure may be varied in many ways. Such variations are not to be regarded as a departure from the scope from the disclosure, and all modifications are intended to be included within the scope of the following claims.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A femoral fracture fixation system comprising:

a femoral intramedullary nail having a posterior side, an anterior side, a proximal portion, a distal portion;

a transverse bore arranged in the proximal portion, the transverse bore including a first and a second recess formed at an inner wall of the transverse bore, wherein the transverse bore has an inlet opening and wherein each of the first and second recess opens out into the inlet opening of the transverse bore, wherein the first recess is arranged on the posterior side and the second recess is arranged on the anterior side of the transverse bore of the intramedullary nail, and wherein the transverse bore has a bore axis and a length along the bore axis, wherein each of the first and second recesses have a conical shape in the direction of the bore axis that defines a length along the inner wall in a direction of the bore axis of the transverse bore and wherein the length of each recess is less than the length of the transverse bore;

a femoral screw slidably received within the transverse bore, the femoral screw having a threaded portion for engaging a head of a femur; and an anti-rotation element moveable along a longitudinal axis of the proximal portion of the nail, and selectively contacting an outer surface of the femoral screw to prevent rotation of the screw.

2. The femoral fracture fixation system according to claim 1, wherein each of the first and second recesses substantially extends in a direction of the bore axis of the transverse bore.

3. The femoral fracture fixation system according to claim 1, wherein the first and second recesses substantially extend from a lateral side to a medial side of the intramedullary nail.

4. The femoral fracture fixation system according to claim 1, wherein the first and second recesses have an oblique extension relative to an extension of the bore axis of the transverse bore.

5. The femoral fracture fixation system according to claim 1, wherein the first and second recesses are concave in cross-section.

6. The femoral fracture fixation system according to claim 1, wherein the first and second recesses define an arc segment in cross-section which extends over an angle (γ) with respect to the bore axis of the transverse bore and wherein the angle (γ) lies between 5° and 175°.

7. The femoral fracture fixation system according to claim 1, wherein the first and second recesses define an arc segment in cross-section and wherein each recess has a width (wr) along the arc segment which lies between 1 mm and 10 mm.

8. The femoral fracture fixation system according to claim 1, wherein the transverse bore defines a first diameter ($d_1$) which is oriented substantially parallel to a longitudinal axis of the proximal portion and a second diameter ($d_2$) which is oriented substantially perpendicular to a longitudinal axis of the proximal portion, wherein the second diameter ($d_2$) is greater than the first diameter ($d_1$) in at least a portion of the transverse bore.

9. The femoral fracture fixation system according to claim 1, wherein the first and second recesses of the transverse bore are arranged adjacent to each other on opposite sides of the bore axis of the transverse bore.

10. The femoral fracture fixation system according to claim 1, wherein the transverse bore has one of flattened and rounded edge portions in a region of at least one of the inlet opening and an outlet opening.

11. The femoral fracture fixation system according to claim 1, wherein the transverse bore of the intramedullary nail bore axis is parallel to or coaxial with a longitudinal axis of the femoral screw.

12. The femoral fracture fixation system according to claim 1, wherein the conical shape defines a taper with a cone angle with respect to the inner wall, wherein the cone angle lies within a plane including the bore axis.

13. A femoral fracture fixation system comprising:

a femoral intramedullary nail having a proximal portion, the proximal portion having a longitudinal axis and an outer surface extending generally parallel to the longitudinal axis;

a circular bore through the proximal portion outer surface extending at an angle to the longitudinal axis of the proximal portion, the proximal portion outer surface having recessed edge surface portions located on at least one side of the bore, the recessed edge surface portions comprising a flattened recessed edge surface portion and a rounded recessed edge surface portion at a screw or pin inlet end, the flattened recessed edge surface portion being flattened along a plane perpendicular to a plane containing both the longitudinal axis of the nail and a central axis of the bore and parallel to the longitudinal axis of the intramedullary nail proximal portion, and the rounded recessed edge surface portion being rounded around an axis transverse to the longitudinal axis and lying in a plane parallel to the plane of the flattened recessed edge surface portion, the circular bore further comprising an anterior and a posterior arc segment which extend into the bore from an opening on a lateral side of the intramedullary nail and tapers inwardly towards a bore axis of the circular bore;

a femoral screw slidably received within the circular bore, the femoral screw having a threaded portion for engaging a head of a femur; and an anti-rotation element moveable along the longitudinal axis of the proximal portion of the nail, and selectively contacting an outer surface of the femoral screw to prevent rotation of the screw.

14. The femoral fracture fixation system as set forth in claim 13 wherein the anterior and posterior arc segments form surfaces of a cone.

15. A femoral fracture fixation system comprising:

a femoral intramedullary nail having a proximal portion, the proximal portion having a longitudinal axis and an outer surface extending generally parallel to the longitudinal axis;

a circular bore through the outer surface extending at an angle to the longitudinal axis of the proximal portion, the proximal portion outer surface having recessed edge surface portions located on at least one side of the bore, the recessed edge surface portions comprising a flattened recessed edge surface portion and a rounded recessed edge surface portion at a screw or pin inlet end, the flattened recessed edge surface portion being flattened along a plane perpendicular to a plane containing both the longitudinal axis of the nail and a central axis of the bore and parallel to the longitudinal axis of the intramedullary nail proximal portion, and the rounded recessed edge surface portion being rounded around an axis transverse to the longitudinal axis and lying in a plane parallel to the plane of the flattened recessed edge surface portion, the circular bore further comprising an anterior and a posterior arc segment which extend into the bore from an opening on a lateral side of the intramedullary nail and tapers inwardly towards a bore axis of the circular bore, wherein the arc segments taper towards the bore axis at an angle of between 1 and 10°;

a femoral screw slidably received within the circular bore, the femoral screw having a threaded portion for engaging a head of a femur; and an anti-rotation element moveable along the longitudinal axis of the proximal portion of the nail, and selectively contacting an outer surface of the femoral screw to prevent rotation of the screw.

16. The femoral fracture fixation system as set forth in claim 15 wherein the anterior and posterior arc segments form surfaces of a cone.

17. The femoral fracture fixation system as set forth in claim 16 wherein the arc segments taper towards the bore axis on moving medially with respect to the bore axis.

* * * * *